(12) United States Patent
Oda et al.

(10) Patent No.: US 6,322,908 B1
(45) Date of Patent: Nov. 27, 2001

(54) ORGANIC ELECTROLUMINESCENT DEVICE

(75) Inventors: Atsushi Oda; Toshiyasu Suzuki; Etsuo Hasegawa, all of Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/225,284

(22) Filed: Jan. 4, 1999

(51) Int. Cl.[7] .................................................... H05B 33/12
(52) U.S. Cl. .......................... 428/690; 428/704; 428/917; 313/504; 313/506
(58) Field of Search ..................................... 428/690, 704, 428/917; 313/504, 506; 252/301.17, 301.21

(56) References Cited

U.S. PATENT DOCUMENTS

| | | | |
|---|---|---|---|
| 4,499,284 | * | 2/1985 | Kosower et al. ...................... 548/359 |
| 4,799,230 | * | 1/1989 | Pavlopoulos et al. ................. 372/53 |
| 5,281,489 | * | 1/1994 | Mori et al. ........................... 428/690 |

FOREIGN PATENT DOCUMENTS

| | | |
|---|---|---|
| 3-200289 | 9/1991 | (JP) . |
| 7-138561 | 5/1995 | (JP) . |
| 8-20771 | 1/1996 | (JP) . |
| 8-40995 | 2/1996 | (JP) . |
| 8-40997 | 2/1996 | (JP) . |
| 8-87122 | 4/1996 | (JP) . |
| 8-239655 | 9/1996 | (JP) . |

OTHER PUBLICATIONS

Florian Pschenitzka et al., "Three–color organic light–emitting diodes patterned by masked dye diffusion", Applied Physics Letters, vol. 74, No. 13, pp. 1913–1915, Mar. 29, 1999.*

* cited by examiner

*Primary Examiner*—Marie Yamnitzky
(74) *Attorney, Agent, or Firm*—Hutchins, Wheeler & Dittmar

(57) ABSTRACT

An organic EL device is disclosed with high brightness and long life, for which a specific compound represented by the formula (I):

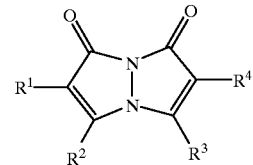

where $R^1$ to $R^4$ each independently represents a hydrogen atom, a halogen atom, an amino group, a hydroxyl group, a cyano group, a nitro group, a substituted or unsubstituted alkyl group, a substituted or unsubstituted cycloalkyl group, a substituted or unsubstituted alkoxy group, a substituted or unsubstituted aromatic hydrocarbon group, a substituted or unsubstituted aromatic heterocyclic group, a substituted or unsubstituted aralkyl group or a substituted or unsubstituted aryloxy group; or $R^1$ to $R^4$ may be coupled together to form a ring is used as a component material.

2 Claims, 1 Drawing Sheet

ORGANIC ELECTROLUMINESCENT DEVICE

BACKGROUND OF THE INVENTION

1. Field of the Invention

This invention relates to an organic electroluminescent device having excellent light emitting properties.

2. Description of the Related Art

An organic electroluminescent device (which will hereinafter be called "organic EL device") is a light emitting device which makes use of the principle that when an electric field is applied, a fluorescent material emits light in response to the charge recombination of holes injected from an anode and electrons injected from a cathode. Since C. W. Tang et al. of Eastman Kodak Company made a report on a low-voltage-driven organic EL device using a double layered structure (C. W. Tang, S. A. Vanslyke, Applied Physics Letters, 51, 913(1987) and the like), studies on an organic EL device and materials have been briskly carried out.

Tang et al. applied tris(8-hydroxyquinolinol)-aluminum to a light emitting layer and a triphenyliamine derivative to a hole transport layer. The laminate structure is accompanied by such advantages as an improvement in the injection efficiency of holes into a light emitting layer; blocking of electrons injected from a cathode, which increases the efficiency of exciton production from charge recombination; and confinement of the excitons into the light emitting layer. As an organic EL device structure, a double layered device composed of a hole injecting and transport layer and an electron transporting and light emitting layer or a triple layered device composed of a hole injecting and transporting layer, a light emitting layer and an electron injecting and transporting layer are well known. In order to increase the recombination efficiency of injected holes and electrons, various improvements in the device structure or fabrication process have been introduced to such a multi-layered device.

As the hole transport material, triphenylamine derivatives such as 4,4', 4"-tris(3-methylphenylphenylamino) triphenylamine known as a starburst molecule and aromatic diamine derivatives such as N,N'-diphenyl-N,N'-bis(3-methylphenyl)-[1,1'-biphenyl]-4,4'-diamine are well known (ex. Japanese Patent Application Laid-Open Nos. 20771/1996, 40995/1996, 40997/1996, 543397/1996 and 87122/1996).

As the electron transporting material, oxadiazole derivatives and triazole derivatives and the like are well known.

As the light emitting material, known are chelate compounds such as tris(8-quinolinolate)aluminum complex, coumarin derivatives, tetraphenylbutadiene derivatives, bis-styrylarylene derivatives, oxadiazole derivatives and the like. Since various color luminescent materials from blue to red region are reported, there is increased expectation for industrialization of a full color organic EL display (ex. Japanese Patent Application Laid-Open Nos. 239655/1996, 138561/1995, 200289/1991 and the like).

In recent days, an organic EL device with high brightness and long life has been disclosed or reported, but it is not always sufficient for manufacturing actual devices yet. Accordingly, there is a strong demand for the development of materials exhibiting high performance.

SUMMARY OF THE INVENTION

An object of the present invention is to provide an organic EL device including a material represented by the formula (I), which potentially has high brightness and long life.

The present inventors have carried out an extensive investigation with a view to resolving the above-described problem. As a result, it has been found that compared with the conventional device, an organic EL device fabricated using a compound represented by the formula (I) as a light emitting material performs with higher brightness and has a longer life when continuously driven. It has also been found that the above-described material has high carrier transporting properties as compared with the conventional device. An organic EL device fabricated using the material as a hole transport material or electron transport material or an organic EL device fabricated using a mixed thin-film of the material and another hole or electron transport material perform with higher brightness and has a longer life when continuously driven, leading to the completion of the invention.

In the present invention, there are thus provided an organic electroluminescent device comprising an anode, a cathode and, between said anode and cathode, one or more than one organic thin-film layers including a light emitting layer, wherein at least one of said layers contains, either singly or as a mixture, a material represented by the following formula (I):

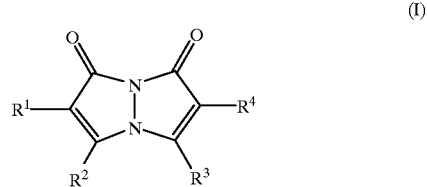

(I)

wherein $R^1$ to $R^4$ each independently represents a hydrogen atom, a halogen atom, an amino group, a hydroxyl group, a cyano group, a nitro group, a substituted or unsubstituted alkyl group, a substituted or unsubstituted cycloalkyl group, a substituted or unsubstituted alkoxy group, a substituted or unsubstituted aromatic hydrocarbon group, a substituted or unsubstituted aromatic heterocyclic group, a substituted or unsubstituted aralkyl group, or a substituted or unsubstituted aryloxy group; or $R^1$ to $R^4$ may be coupled together to form a ring; and the above-described organic electroluminescent device having a hole transport layer or electron transport layer as one of the organic thin-film layers, wherein said hole transport layer or electron transport layer contains the compound of the above-described formula (I) singly or as a mixture.

The use of the compound according to the present invention as a component material of an organic EL device makes it possible to provide light emission with higher brightness compared with the conventional device. Thus, the present invention brings about marked effects.

LEGENDS

Figure 1:
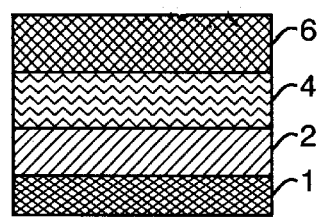
FIG. 1 is a schematic cross-sectional view illustrating the device of the present invention (Example 1)

1: Substrate 2: Anode 3: Hole transport layer 4: Light Emitting layer 5: Electron transport layer 6: Cathode.

DETAILED DESCRIPTION OF THE EMBODIMENTS

The embodiments of the present invention will hereinafter be described specifically.

The compound of the present invention is a compound having a structure represented by the formula (I). In the formula (I), $R^1$ to $R^4$ each independently represents a hydrogen atom, a halogen atom, an amino group, a hydroxyl group, a cyano group, a nitro group, a substituted or unsubstituted alkyl group, a substituted or unsubstituted cycloalkyl group, a substituted or unsubstituted alkoxy group, a substituted or unsubstituted aromatic hydrocarbon group, a substituted or unsubstituted aromatic heterocyclic group, a substituted or unsubstituted aralkyl group or a substituted or unsubstituted aryloxy group; or $R^1$ to $R^4$ may be coupled together to form a ring.

Example of the halogen atom include fluorine, chlorine, bromine and iodine.

Examples of the substituted or unsubstituted alkyl group include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl groups.

Example of the substituted and unsubstituted cycloalkyl group include cyclopropyl, cyclobutyl, cyclopentyl, cyclohexyl and 4-methylcyclohexyl groups.

Example of the substituted and unsubstituted aromatic hydrocarbon group include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl groups.

Examples of the substituted or unsubstituted aromatic heterocyclic group include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-3-butyl-3-indolyl groups.

Example of the ring-forming divalent group include tetramethylene, pentamethylene, hexamethylene, diphenylmethane-2,2'-diyl, diphenylethane-3,3'-diyl and diphenylpropane-4,4'-diyl groups.

Example of the alkoxy group include methoxy, ethoxy, propoxy, isopropoxy, n-butoxy, s-butoxy, isobutoxy, n-hexyloxy and cyclohexyloxy groups.

The substituted or unsubstituted alkoxy group is a group represented by -OX. Examples of X include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl groups.

Examples of the substituted or unsubstituted aralkyl group include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2- (1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl groups.

The substituted or unsubstituted aryloxy group is represented by -OY. Examples of the Y include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl) phenyl, 3-methyl-2-naphthyl, 4-methyl-1-naphthyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl groups.

Compounds represented by the below-described formulas (1) to (16) will next be indicated as the examples of the compound of the present invention, but it should however be borne in mind that the present invention is not limited to them.

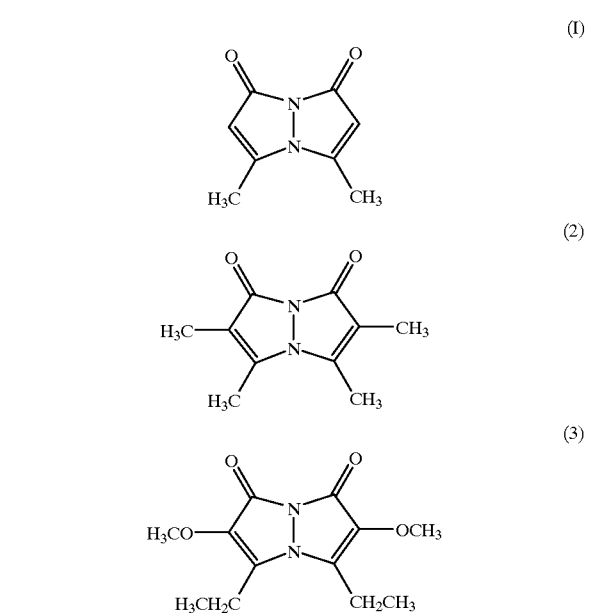

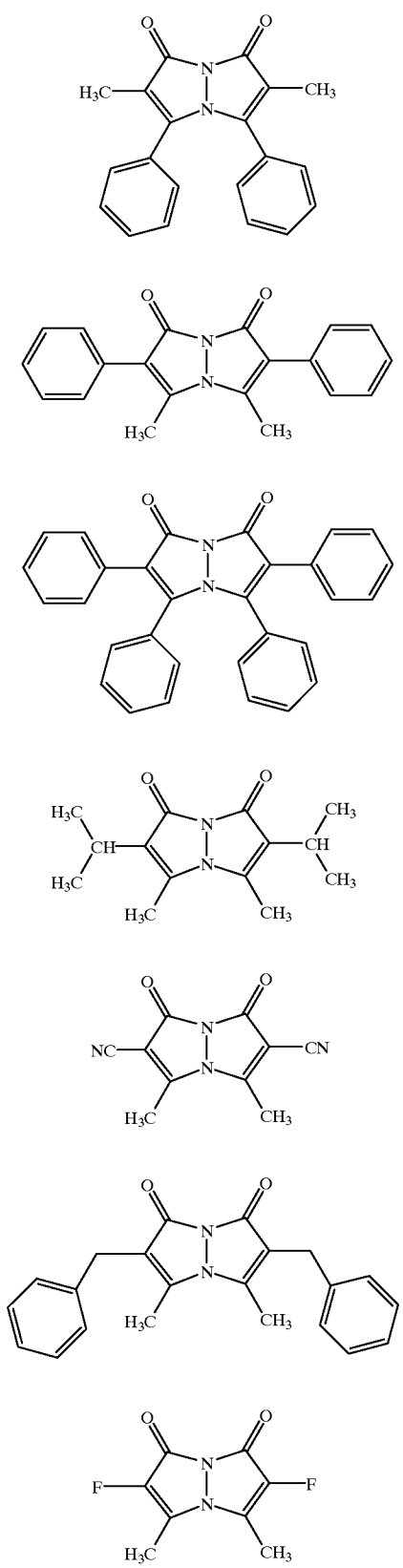

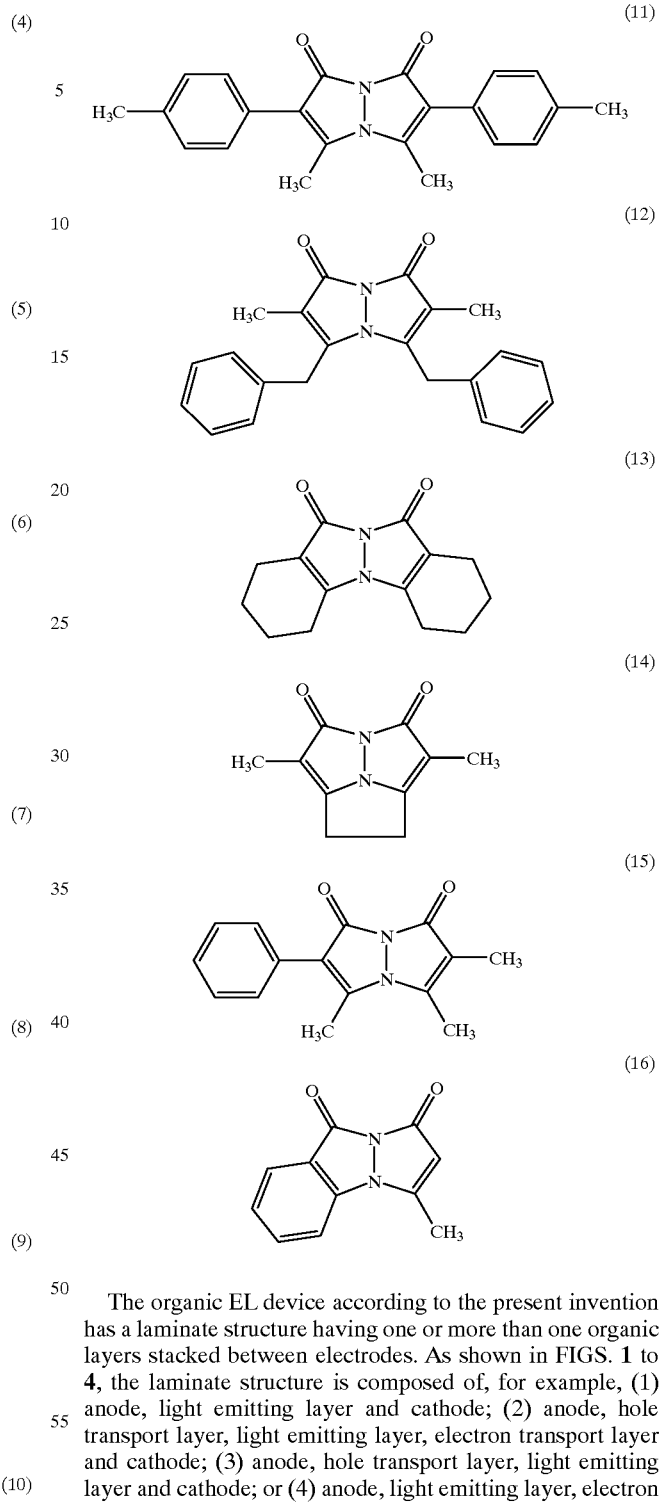

The organic EL device according to the present invention has a laminate structure having one or more than one organic layers stacked between electrodes. As shown in FIGS. 1 to 4, the laminate structure is composed of, for example, (1) anode, light emitting layer and cathode; (2) anode, hole transport layer, light emitting layer, electron transport layer and cathode; (3) anode, hole transport layer, light emitting layer and cathode; or (4) anode, light emitting layer, electron transport layer and cathode.

The compound of the present invention may be contained in any one of the above-described organic layers. It is also possible to dope the compound into another hole transport material, light emitting material or electron transport material.

There is no particular limitation imposed on the hole transport material to be used in the present invention. Any compound employed as an ordinary hole transport material may be used. Examples include triphenyldiamines such as bis(di(p-tolyl)aminophenyl)-1,1-cyclohexane [01], N,N'-diphenyl-N,N'-bis(3-methylphenyl)-1,1'-biphenyl-4,4'-diamine [02] and N,N'-diphenyl-N-N-bis(1-naphthyl)-1,1'-biphenyl)-4,4'-diamine [03] and starburst type molecules ([04] to [06]). They are represented by the following formulas [01] to [06], respectively.

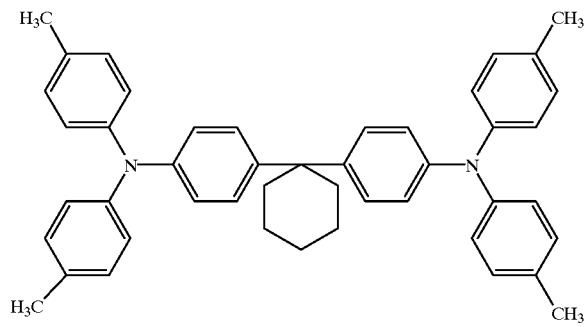

[01]

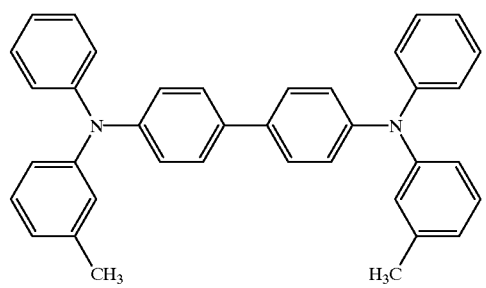

[02]

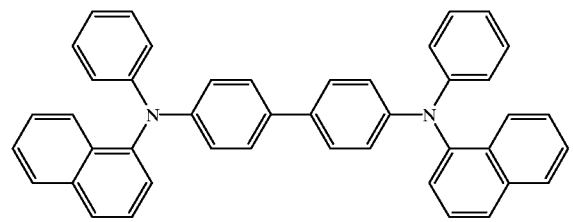

[03]

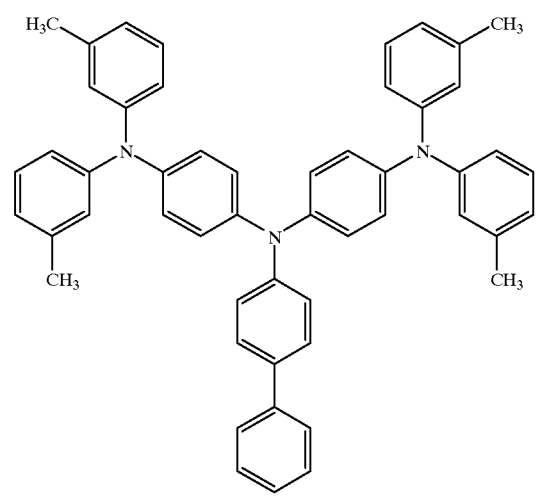

[04]

[05]

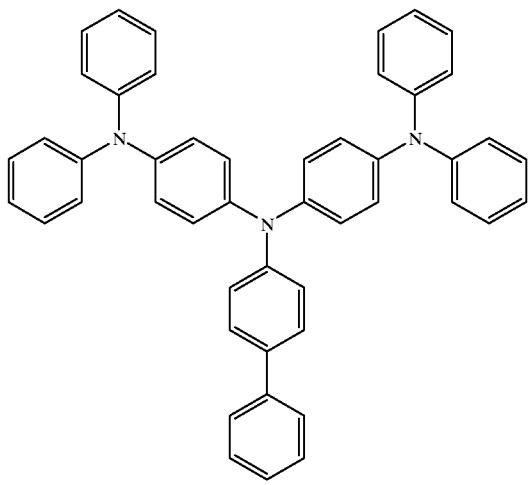

[06]

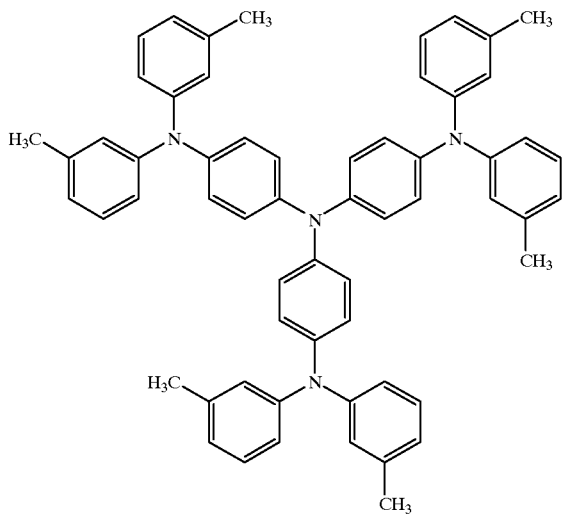

There is no particular limitation imposed on the electron transport material to be used in the present invention. Any material employed ordinarily as an electron transport material can be employed. Examples include oxadiazole derivatives such as 2-(4-biphenylyl)-5-(4-t-butylphenyl)-1,3,4-oxadiazole [07] and bis{2-(4-t-butylphenyl)-1,3,4-oxadiazole}-m-phenylene [08], triazole derivatives ([09], [10] and the like) and quinolinol type metal complexes ([11] to [14] and the like). They are represented by the formulas [07] to [14], respectively.

[07]

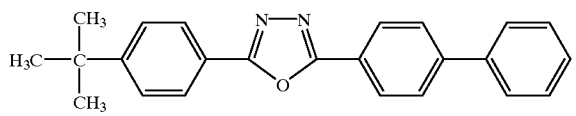

[08]

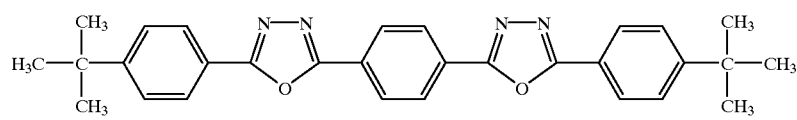

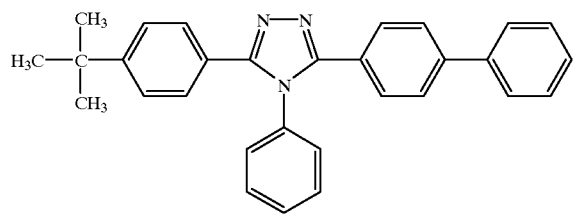
[09]
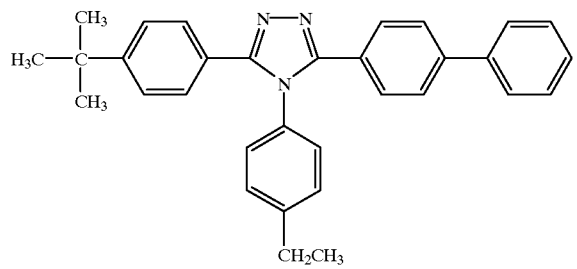
[10]
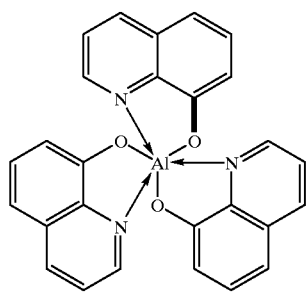
[11]
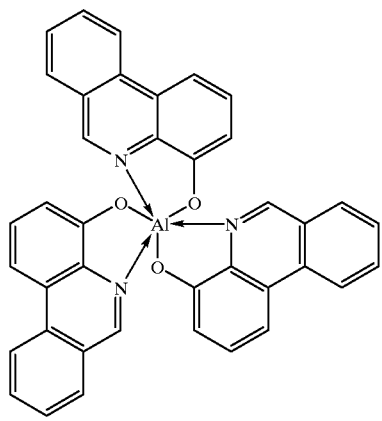
[12]
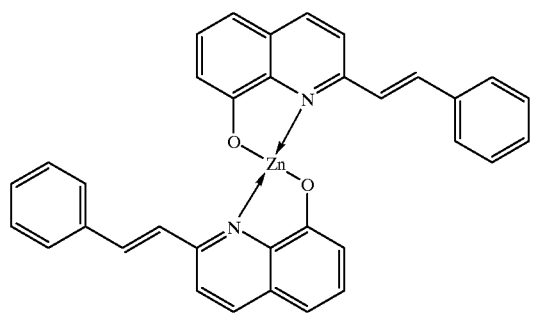
[13]

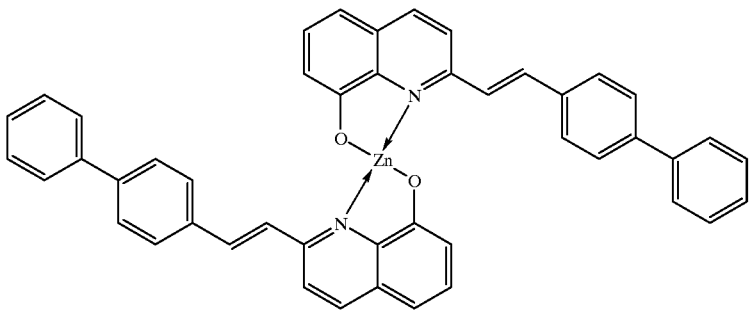
[14]

The anode of the organic thin-film EL device plays a role of injecting holes into the hole transport layer and that having a work function of 4.5 eV or greater is effective.

Specific examples of the anode material to be used in the present invention include an indium tin oxide (ITO), tin oxide (NESA), gold, silver, platinum and copper.

For effective injection of electrons into the electron transport layer or light emitting layer, the cathode having a smaller work function is preferred.

Although there is no particular limitation imposed on the cathode material, specific examples include indium, aluminum, magnesium, magnesium-indium alloy, magnesium-aluminum alloy, aluminum-lithium alloy, aluminum-scandium-lithium alloy and magnesium-silver alloy.

There is no particular limitation imposed on the forming method of each layer of the organic EL device accord in g to the present invention. Conventionally known methods such as vacuum deposition and spin coating can be employed. The organic thin-film layer which is to be used in the organic EL device of the present invention and contains the compound of the formula (1) can be formed by a known method such as vacuum deposition, molecular beam evaporation (MBE) or coating of a solution of the compound in a solvent such as dipping, spin coating, casting, bar coating or roll coating.

There is no particular limitation imposed on the thickness of each of the organic layers of the organic EL device of the present invention. When the film is too thin, however, defects such as pin holes tend to occur. When the film is too thick, on the other hand, a high applied voltage is required, which deteriorates the efficiency. Usually, the organic layers are therefore preferred to have a film thickness within a range of several nm to 1 μm.

EXAMPLES

The present invention will hereinafter be described in detail by examples, but it should however be borne in mind that the present invention is not limited only to the following examples so long as they do not depart from the spirit or scope of the invention.

Synthesis Example

The compound of the present invention can be synthesized by the conventionally known process (for example, E. M. Kosower, B. Pazhenchevsky, Journal of American Chemical Society, 102, 4938(1980)).

Compound [1] can be obtained, for example, by reacting an acetoacetate ester derivative with hydrazine to obtain 3,4-di-substituted-2-pyrazolin-5-one, reacting the resulting product with chlorine to obtain 3,4-di-substituted-4-chloro-2-pyrazolin-5-one and then treating the thus-synthesized product with a base. The compound will next be indicated by the number with reference to Tables 1 and 2.

Synthesis Example 1

Synthesis of 3,4,6,7-tetramethyl-1,5-diazabicyclo[3,3,0]octa-3,5-diene-2,8-dione (Compound (2))

To a solution of ethyl 2-methylacetoacetate in ethanol, excess hydrazine was added, followed by heating for 1 hour. After the reaction, the reaction mixture was cooled and recrystallized from a 1:1 mixture of benzene and petroleum ether, whereby 3,4-dimethyl-2-pyrazolin-5-one was obtained.

A chlorine gas was introduced into a solution of 3,4-dimethyl-2-pyrazolin-5-one in 1,2-dichloroethane, followed by gradual refluxing. After the reaction, the reaction mixture was cooled and filtered. The solvent was then distilled off. The residue in the form of an oil was recrystallized from a 1:1 mixture of benzene and petroleum ether, whereby 3,4-dimethyl-4-chloro-2-pyrazolin-5-one was obtained.

A solution of 3,4-dimethyl-4-chloro-2-pyrazolin-5-one in dichloromethane was added dropwise to a suspension of a mixture of potassium carbonate hydrate and potassium carbonate in dichloromethane, which suspension had been cooled to 0° C., followed by stirring at 0° C. for 2 hours and then at room temperature for 10 hours. After the reaction, the reaction mixture was filtered. The filtrate was concentrated with evapolator and recrystallized from acetonitrile, whereby 3,4,6,7-tetramethyl-1,5-diazabicyclo[3,3,0]octa-3,5-dien-2,8-dione was obtained.

Synthesis Examples 2 to 14

Synthesis of Compound (1) and Compounds (3) to (14)

In a similar manner to Synthesis Example 1 except for the use of compounds as shown in Table 1 instead of ethyl 2-methylacetoacetate, Compounds (1) and Compounds (3) to (14) were synthesized.

Synthesis Example 15

Synthesis of 3,4,6-trimethyl-7-phenyl-1,5-diazabicyclo[3,3,0]octa-3,5-dien-2,8-dione
(Compound (15))

In a similar manner to Synthesis Example 1, 3-methyl-4-phenyl-4-chloro-2-pyrazolin-5-one and 3,4-dimethyl-4- chloro-2-pyrazolin-5-one were obtained from ethyl 2-phenylacetoacetate and ethyl 2-methylacetoacetate, respectively.

A solution of a mixture of the reaction products in dichloromethane was added dropwise to a suspension of potassium carbonate hydrate and potassium carbonate in dichloromethane, followed by stirring at 0° C. for 2 hours and then at room temperature for 10 hours. After the reaction, the reaction mixture was filtered. The filterate was concentrated with evapolator and recrystallized from acetonitrile solution, whereby 3,4,6-trimethyl-7-phenyl-1,5-diazabicyclo[3,3,0]octa-3,5-diene-2,8-dione was obtained.

Synthesis Example 16

Synthesis of Compound (16)

In a similar manner to Synthesis Example 15 except for the use of the compounds shown in Table 2 instead of ethyl 2-phenylacetoacetate and ethyl 2-methylacetoacetate, Compound (16) was obtained.

TABLE 1-a

| compound | ethyl acetoacetate derivative | compound [1] |
|---|---|---|
| (1) | Me-CO-CH(H)-CO-OEt | R¹=H, R²=Me (H, H on top; Me, Me on bottom) |
| (2) | Me-CO-CH(Me)-CO-OEt | R¹=Me, R²=Me |
| (3) | Et-CO-CH(OMe)-CO-OEt | R¹=OMe, R²=Et |
| (4) | Ph-CO-CH(Me)-CO-OEt | R¹=Me, R²=Ph |
| (5) | Me-CO-CH(Ph)-CO-OEt | R¹=Ph, R²=Me |
| (6) | Ph-CO-CH(Ph)-CO-OEt | R¹=Ph, R²=Ph |

TABLE 1-a-continued
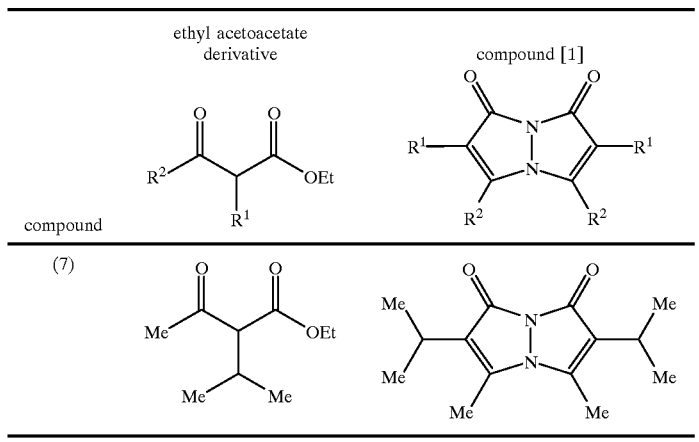
TABLE 1-b
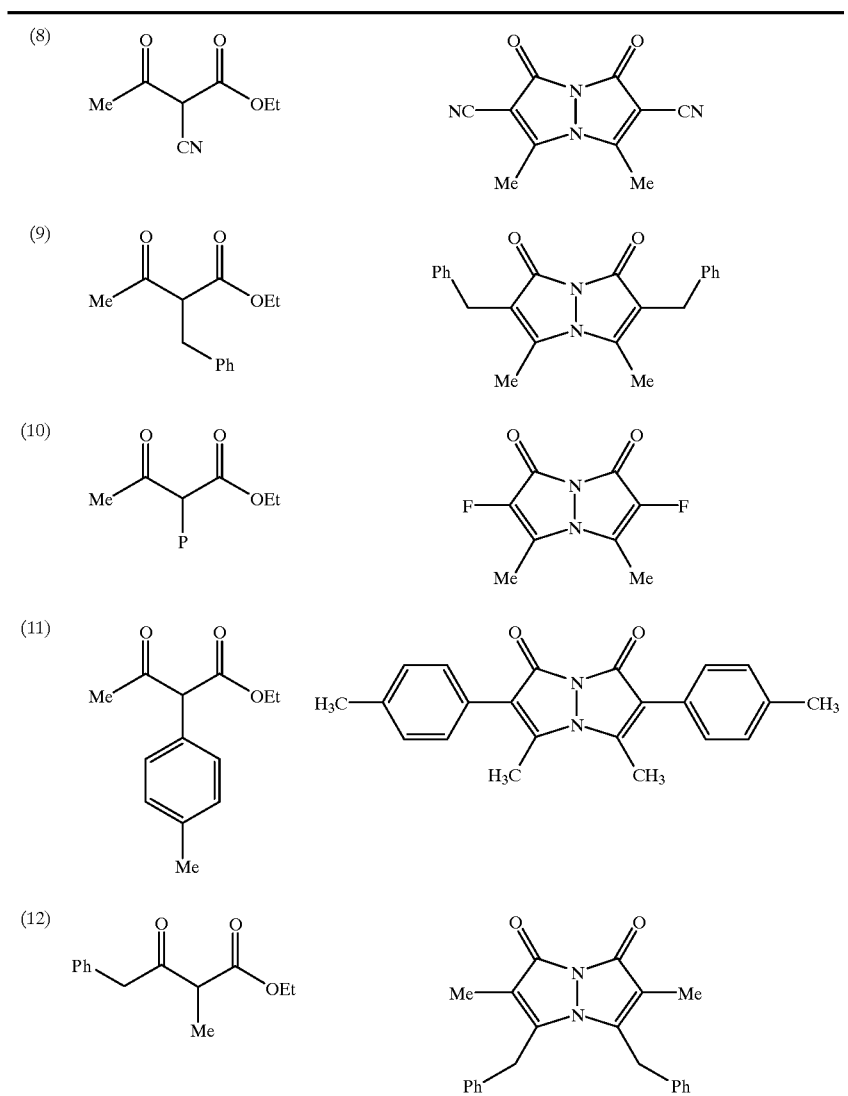

TABLE 1-b-continued

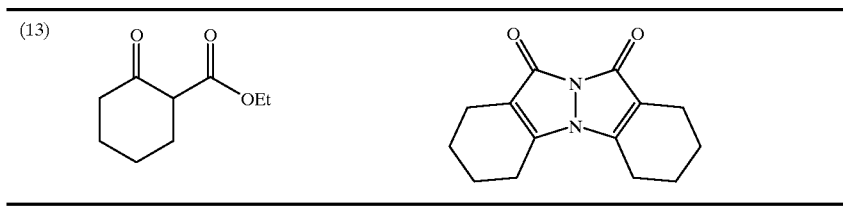

TABLE 2

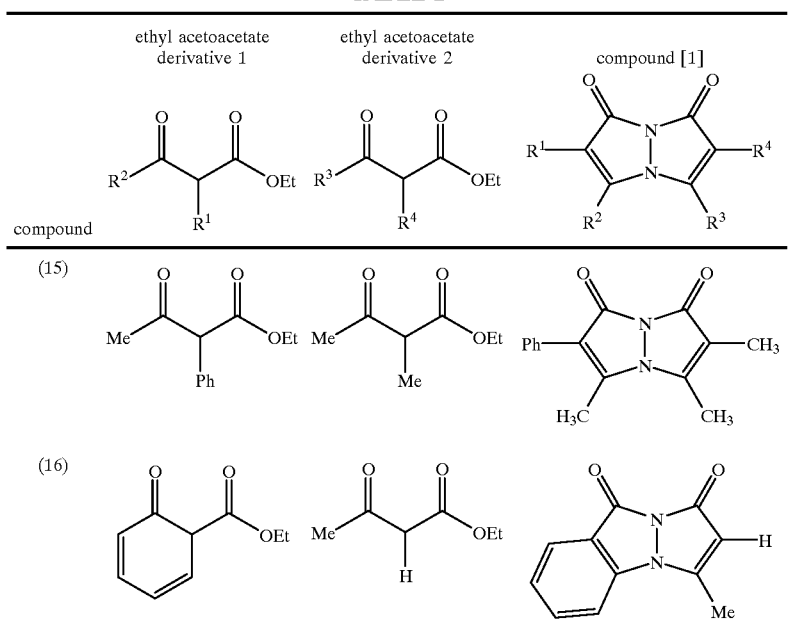

A description will be made of following examples wherein the invention compound is used as a light emitting layer (Examples 1 to 7), a mixed thin-film of the invention compound with a hole transport material is used as a light emitting layer (Examples 8 to 10), a mixed thin-film of the invention compound with an electron transport material is used as a light emitting layer (Examples 11 to 12), the invention compound is used as a hole transport layer (Examples 13 to 14) and the invention compound is used as an electron transport layer (Example 15).

Example 1

FIG. 1 illustrates the cross-sectional structure of the device in Example 1. The fabrication procedure of the organic thin-film EL device in Example 1 of the present invention will be described. The device is composed of an anode, light emitting layer and cathode.

ITO was sputtered on a glass substrate to form a film having a sheet resistance of 20 ohm/square as the anode. Over the anode, 40 nm thickness of compound (1) was vacuum deposited as a light emitting layer. Then, the cathode of a magnesium-silver alloy was vacuum deposited to 150 nm thickness, whereby the organic EL device was fabricated.

When a dc voltage of 5V was applied to the device, violet light emission of 85 $cd/m^2$ was obtained.

Example 2

In a similar manner to Example 1 except for the use of Compound (13) as a light emitting material, an organic EL device was fabricated. When a dc voltage of 5V was applied to the device, blue light emission of 150 $cd/m^2$ was obtained.

Example 3

ITO was sputtered on a glass substrate to form a film having a sheet resistance of 20 ohm/square as an anode. Over the anode, a solution obtained by dissolving 3 wt. % of Compound (3) in N,N-dimethylformamide was applied by spin coating, whereby a light emitting layer of 100 nm was formed. Then, a cathode was formed to 150 nm thickness by the vacuum deposition of a magnesium-silver alloy, whereby an organic EL device was fabricated.

When a dc voltage of 10V was applied to the device, blue light emission of 90 $cd/m^2$ was obtained.

Example 4

Figure 2:
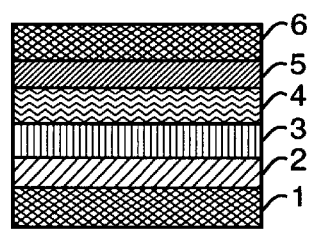
FIG. 2 is a schematic cross-sectional view illustrating the device of the present invention (Example 4)

FIG. 2 illustrates the cross-sectional structure of a device in Example 4. The device is composed of an anode, a hole transport layer, a light emitting layer, an electron transport layer and a cathode. ITO was sputtered on a glass substrate to form a film having a sheet resistance of 20 ohm/square as an anode.

Over the anode, the hole transport layer was formed to 50 nm by the vacuum deposition of N,N'-diphenyl-N,N'-bis(3-methylphenyl)-[1,1'-biphenyl]-4,4'-diamine [02].

Then, the light emitting layer was formed to 40 nm by the vacuum deposition of Compound (2), followed by the formation of the electron transport layer to 20 nm by the vacuum deposition of 2-(4-biphenyl)-5-(4-t-butylphenyl)-1,3,4-oxadiazole [07].

The cathode was then formed to 150 nm by the vacuum deposition of a magnesium-silver alloy, whereby an organic EL device was fabricated.

When a dc voltage of 10V was applied to the device, blue light emission of 2000 cd/m$^2$ was obtained.

Example 5

In a similar manner to Example 4 except for the use of N,N'-diphenyl-N-N-bis(1-naphthyl)-1,1'-biphenyl)-4,4'-diamine [03] as the hole transport layer, Compound (5) as the light emitting layer and bis{2-(4-t-butylphenyl)-1,3,4-oxadiazole}-m-phenylene [08] as the electron transport layer, an organic EL device was fabricated.

When a dc voltage of 10V was applied to the device, blue light emission of 2500 cd/m$^2$ was obtained.

Example 6

In a similar manner to Example 4 except for the use of [04] as the hole transport layer, Compound (6) as the light emitting layer and [11] as the electron transport layer, an organic EL device was fabricated. When a dc voltage of 10V was applied to the device, bluish green light emission of 2800 cd/m$^2$ was obtained.

Example 7

In a similar manner to Example 4 except for the use of [05] as the hole transport layer, Compound (7) as the light emitting layer and [12] as the electron transport layer, an organic EL device was fabricated. When a dc voltage of 10V was applied to the device, blue light emission of 2100 cd/m$^2$ was obtained.

Example 8

In a similar manner to Example 4 except for the use of [04] as the hole transport layer, Compound (9) as the light emitting layer and [09] as the electron transport layer, an organic EL device was fabricated. When a dc voltage of 10V was applied to the device, blue light emission of 2400 cd/m$^2$ was obtained.

Example 9

Figure 4:
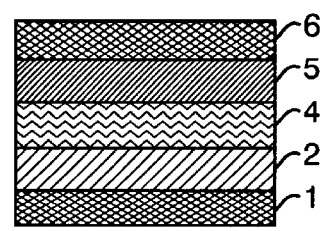
FIG. 4 is a schematic cross-sectional view illustrating the device of the present invention (Example 9).

FIG. 4 illustrates the cross-sectional structure of a device in Example 9. The device is composed of an anode, a light emitting layer, an electron transport layer and a cathode. ITO was sputtered on a glass substrate to form a film having a sheet resistance of 20 ohm/square as an anode.

Over the anode, a thin-film was formed to 50 nm as the emitter layer by the co-deposition of N,N'-diphenyl-N-N-bis(1-naphthyl)-1,1'-biphenyl)-4,4'-diamine [03] and Compound (4) at a weight ratio of 1:10. The electron transport layer was then formed to 50 nm by the vacuum deposition of [09], followed by the formation of the cathode to 150 nm by the vacuum deposition of a magnesium-silver alloy, whereby the EL device was fabricated.

When a dc voltage of 10V was applied to the device, blue light emission of 1200 cd/m$^2$ was obtained.

Example 10

In a similar manner to Example 8 except for the use of Compound (16) instead of Compound (9), an organic EL device was fabricated. When a dc voltage of 10V was applied to the device, blue light emission of 1300 cd/m$^2$ was obtained.

Example 11

ITO was sputtered on a glass substrate to form a film having a sheet resistance of 20 ohm/square as an anode. Over the anode, a light emitting layer of 100 nm was formed by the spin coating of an N,N-dimethylformamide solution containing Compound (11) and N,N'-diphenyl-N-N-bis(1-naphthyl) -1,1'-biphenyl) -4,4'-diamine [03] at a molar ratio of 1:10.

The electron transport layer of 50 nm was then formed by the vacuum deposition of [10], followed by the formation of a cathode thereover to 150 nm by the vacuum deposition of a magnesium-silver alloy, whereby an organic EL device was fabricated.

When a dc voltage of 10V was applied to the device, blue light emission of 700 cd/m$^2$ was obtained.

Example 12

Figure 3:
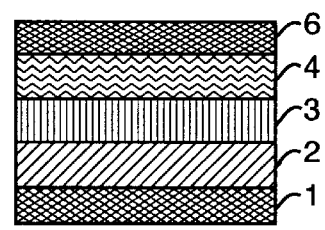
FIG. 3 is a schematic cross-sectional view illustrating the device of the present invention (Example 12)

FIG. 3 illustrates the cross-sectional structure of a device in Example 12. The device is composed of an anode, hole transport layer, light emitting layer and cathode. ITO was sputtered on a glass substrate to form a film having a sheet resistance of 20 ohm/square as the anode. Over the anode, the hole transport layer was formed to 50 nm by the vacuum deposition of Compound [04].

A film was then formed to 50 nm as the light emitting layer by the vacuum co-deposition of [07] and Compound (10) at a weight ratio of 20:1, followed by the formation of the cathode to 150 nm by the vacuum deposition of a magnesium-silver alloy, whereby the EL device was fabricated.

When a dc voltage of 10V was applied to the device, blue light emission of 1500 cd/m$^2$ was obtained.

Example 13

In a similar manner to Example 11 except for the use of N,N'-diphenyl-N,N'-bis(3-methylphenyl)-[1,1'-biphenyl]-4,4'-diamine [02] as the hole transport layer and a film formed as the light emitting layer by the vacuum co-deposition of [13] and Compound (12) at a weight ratio of 20:1, an organic EL device was fabricated.

When a dc voltage of 10V was applied to the device, yellow light emission of 1700 cd/m$^2$ was obtained.

Example 14

In a similar manner to Example 4 except for the use of Compound (5) as the hole transport layer and [13] as the light emitting layer, an organic EL device was fabricated. When a dc voltage of 10V was applied to the device, yellow light emission of 1300 cd/m$^2$ was obtained.

Example 15

In a similar manner to Example 4 except for the use of Compound (15) as the hole transport layer and [13] as the light emitting layer, an organic EL device was fabricated. When a dc voltage of 10V was applied to the device, yellow light emission of 1100 cd/m$^2$ was obtained.

Example 16

In a similar manner to Example 4 except for the use of N,N'-diphenyl-N-N-bis(1-naphthyl)-1,1'-biphenyl)-4,4'-diamine [03] as the hole transport layer, [13] as the light emitting layer and Compound (8) as the electron transport layer, an organic EL device was fabricated.

When a dc voltage of 10V was applied to the device, yellow light emission of 1800 cd/m² was obtained.

Example 17

In a similar manner to Example 4 except for the use of N,N'-diphenyl-N-N-bis(1-naphthyl)-1,1'-biphenyl)-4,4'-diamine [03] as the hole transport layer, [13] as the light emitting layer and Compound (10) as the electron transport layer, an organic EL device was fabricated. When a dc voltage of 10V was applied to the device, yellow light emission of 2000 cd/m² was obtained.

What is claimed is:

1. An organic electroluminescent device comprising an anode, a cathode and, between said anode and cathode, one or more organic thin-film layers including a light emitting layer, wherein at least one of said organic thin-film layers contains a material represented by the formula (I):

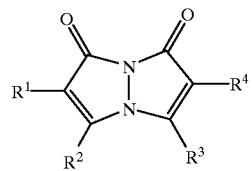

wherein $R^1$ to $R^4$ each independently represents a hydrogen atom, a halogen atom, an amino group, a hydroxyl group, a cyano group, a nitro group, a substituted or unsubstituted alkyl group, a substituted or unsubstituted cycloalkyl group, a substituted or unsubstituted alkoxy group, a substituted or unsubstituted aromatic hydrocarbon group, a substituted or unsubstituted aromatic heterocyclic group, a substituted or unsubstituted aralkyl group, or a substituted or unsubstituted aryloxy group; or $R^1$ to $R^4$ may be coupled together to form a ring, wherein said organic thin-film layers further comprise at least one hole transport layer and said hole transport layer contains the compound of the formula (I) either singly or as a mixture.

2. An organic electroluminescent device comprising an anode, a cathode and, between said anode and cathode, one or more organic thin-film layers including a light emitting layer, wherein at least one of said organic thin-film layers contains a material represented by the formula (I):

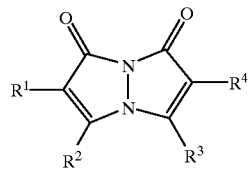

wherein $R^1$ to $R^4$ each independently represents a hydrogen atom, a halogen atom, an amino group, a hydroxyl group, a cyano group, a nitro group, a substituted or unsubstituted alkyl group, a substituted or unsubstituted cycloalkyl group, a substituted or unsubstituted alkoxy group, a substituted or unsubstituted aromatic hydrocarbon group, a substituted or unsubstituted aromatic heterocyclic group, a substituted or unsubstituted aralkyl group, or a substituted or unsubstituted aryloxy group; or $R^1$ to $R^4$ may be coupled together to form a ring, wherein said organic thin-film layers further comprise at least one electron transport layer and said electron transport layer contains the compound of the formula (I) either singly or as a mixture.

* * * * *